United States Patent [19]

Dragan

[11] 4,106,374
[45] Aug. 15, 1978

[54] ORTHODONTIC O-RING DISPENSER AND LIGATOR THEREFOR

[76] Inventor: William B. Dragan, R.F.D. #1 Burr St., Fairfield, Conn. 06430

[21] Appl. No.: 631,920

[22] Filed: Nov. 14, 1975

Related U.S. Application Data

[63] Continuation-in-part of Ser. No. 423,420, Dec. 10, 1973, abandoned.

[51] Int. Cl.² .............................................. B25B 7/12
[52] U.S. Cl. ...................................... 81/302; 221/36; 221/312 A; 32/66
[58] Field of Search ................... 221/312, 63, 279, 39, 221/40, 56, 36, 226, 312 A; 312/42, 71; 229/17; 206/820, 339, 343, 338, 303; 29/268, 227; 81/302

[56] References Cited

U.S. PATENT DOCUMENTS

| | | | |
|---|---|---|---|
| 2,519,024 | 8/1950 | Collett | 81/302 |
| 2,709,937 | 6/1955 | McVey | 81/302 |
| 3,092,287 | 6/1963 | Erdmann | 221/312 R |
| 3,412,897 | 11/1968 | Slater | 221/226 |
| 3,416,650 | 12/1968 | Mortensen | 206/338 |
| 3,623,635 | 11/1971 | Erdmann | 221/312 A |
| 3,654,755 | 4/1972 | Bell | 81/302 |

*Primary Examiner*—James L. Jones, Jr.
*Attorney, Agent, or Firm*—Arthur T. Fattibene

[57] ABSTRACT

An orthodontic O-ring dispenser comprising a magazine or housing for containing a supply of stacked O-rings that are progressively advanced toward a slotted discharge opening wherein the respective O-rings are individually dispensed by stretching the endmost O-ring with the aid of a ligator to permit the dispensing of the O-ring through the discharge opening. The O-ring dispenser may also comprise a plurality of O-rings integrally molded to a core and which are connected thereto in a manner to facilitate the independent removal of the respective O-rings from the attached core.

9 Claims, 16 Drawing Figures

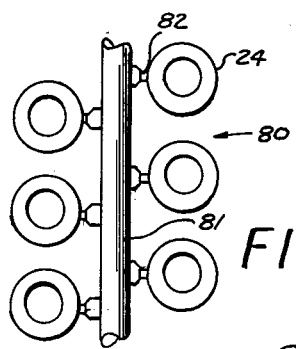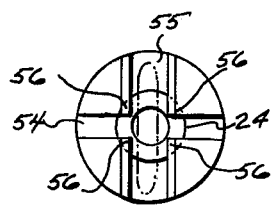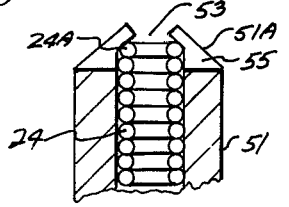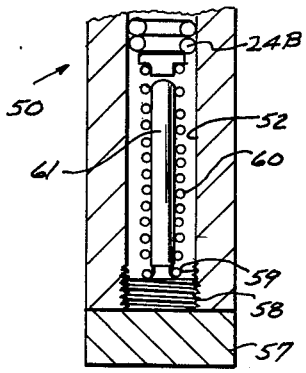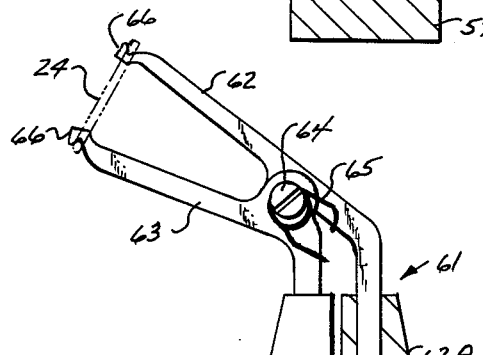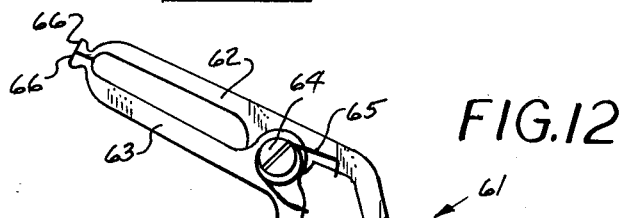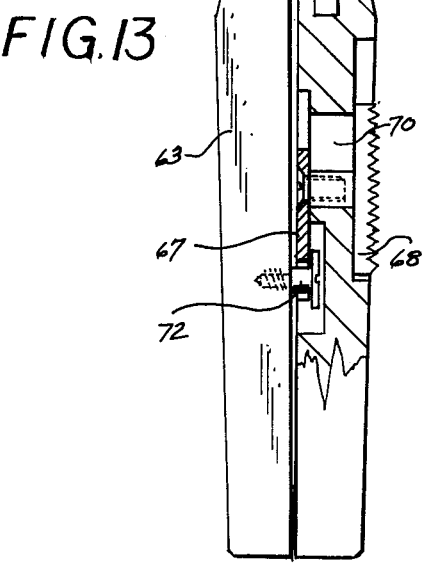

ORTHODONTIC O-RING DISPENSER AND LIGATOR THEREFOR

This is a continuation-in-part of application Ser. No. 423,420 filed Dec. 10, 1973, now abandoned for Orthodontic O-Ring Dispenser and Ligator Therefor.

PROBLEM AND PRIOR ART

The esthetics during orthodontic treatment have been greatly improved by the technique of adhering directly to the patient's teeth a bracket, which may be formed of either metal or plastic and the attachment thereto of a resilient wire for exerting on the teeth the required force needed for straightening or shifting of the teeth as may be required. It is the present practice to utilize small O-rings made of an elastic material for attaching the wire to the respective brackets.

Heretofore such O-rings were randomly packaged, and because of their size and randomly packaged arrangements considerable difficulty has been encountered in the handling and placing of such O-rings onto the brackets to hold the wire in place with respect thereto. The practice heretofore in placing such O-rings onto the teeth brackets generally consisted of the orthodontist "fishing" for the O-rings with a probe and with the use of such probe stretching the O-ring over the bracket to secure the wire. Such procedure was relatively primitive, time consuming, and wasteful as many O-rings would be frequently dropped and lost in effecting the removal thereof from the box or source of supply and the placement thereof onto the patient's teeth bracket. As this technique of straightening teeth required the application of a relatively large number of such O-rings, it is readily apparent that the application of such O-rings is a tedious and time consuming task.

OBJECTS

An object of this invention resides in the provision or an orthodontic O-ring dispenser which is simple in construction, which can be inexpensively manufactured and which is positive in operation.

Another object is to provide an orthodontic O-ring dispenser in which the O-rings can be readily dispensed and applied to a patient's mouth with the aid of a ligator.

Another object is to provide an orthodontic O-ring dispenser and loader therefor.

Another object is to provide for an orthodontic O-ring dispenser in which the plurality of individual O-rings are integrally molded as a unitary item in a manner whereby the respective O-rings can be individually dispensed.

Another object resides in the provision of a ligator for facilitating the dispensing and application of the O-ring to a patient's mouth.

BRIEF SUMMARY OF THE INVENTION

One embodiment of an orthodontic O-ring dispenser comprises a tubular housing having a bore extending therethrough to define a magazine for containing a supply of stacked O-rings. One end of the housing is provided with a transversely extending slot which extends across the bore to define a discharge opening. The transverse slot is formed to provide interned lips which function as a stop for the stacked O-rings which prohibit the O-rings from passing through the discharged opening. The other end of the bore is closed by a cap or closure. A means is provided for exerting a pressure on the stacked O-rings for progressively advancing the O-rings toward the dispensing opening as the endmost O-ring is dispensed.

To effect dispensing of the endmost O-ring, a ligator is provided. The ligator comprises a tool having relatively moveable jaws which are shaped to be inserted into the discharge slotted opening to hook the endmost O-ring, and upon the opening of the jaws the endmost O-ring is stretched or distorted so that it can be readily released from the slotted discharge opening. With the discharge O-ring stretched onto the ligator, it can be readily applied to the patient's mouth by the dentist. In one form of the invention the ligator is provided with a lock to maintain the jaws in the opened position so that the O-ring can be held in a stretched position for an indefinite period of time automatically.

To facilitate the loading of O-rings into the magazine of the dispenser, there is provded a loader. The loader comprises a rod or shaft on which the O-rings are preloaded. The loader with the O-rings loaded thereon is simply placed in the magazine of the dispenser and the rod or shaft is pulled through the dispensing opening free of the O-rings which are retained in the magazine.

Another form of the invention contemplates an integrally formed dispenser in which the respective O-rings are integrally molded to a core or tree in a manner wherein the respective O-rings are releasably connected to the core or tree wherein the respective O-rings can be removed as desired.

FEATURES

A feature of this invention resides in the provision of an orthodontic O-ring dispenser in which the O-rings can be expeditiously dispensed in a minimum of time and with a minimum of effort.

Another feature of the invention resides in an orthodontic O-ring dispenser in which the O-rings can be individually dispensed with the aid of a ligator in a manner wherein the O-ring upon being dispensed is in position on a tool which is readied for direct application of the O-ring to the patient's mouth.

Another feature resides in the provision of an orthodontic O-ring dispenser and loader therefor whereby the O-rings can be readily positioned in the dispenser.

Another feature resides in the provision of an improved ligator for facilitating the removal of the O-ring from the dispenser and the placement of the O-ring onto the bracket attached to a patient's tooth.

Another feature of the invention resides in the provision wherein the orthodontic O-rings dispensing arrangement is one in which the O-rings are integrally formed.

Other features and advantages will become more readily apparent when considered in view of the drawings and specification in which:

FIG. 9 is a sectional elevation view of a modified orthodontic O-ring dispenser embodying the present invention.

FIG. 10 is a sectional elevation view similar to that of FIG. 9 illustrating the relative position of the component parts after a number of O-rings have been dispensed therefrom.

FIG. 11 is an end view of the dispensing opening of the orthodontic O-ring dispenser illustrated in FIGS. 9 and 10.

FIG. 12 is a side view of a modified ligator construction for effecting the removal of the O-ring through the dispensing opening of the orthodontic O-ring dispenser and for applying the O-ring to a patient's mouth.

FIG. 13 is a side elevation of the ligator shown in FIG. 12 but illustrated in the latched or locked position.

FIG. 14 illustrates another embodiment for dispensing orthodontic O-rings.

FIG. 15 is a fragmentary detailed view taken along lines 15—15 on FIG. 12.

DETAILED SPECIFICATION

Figure 1:
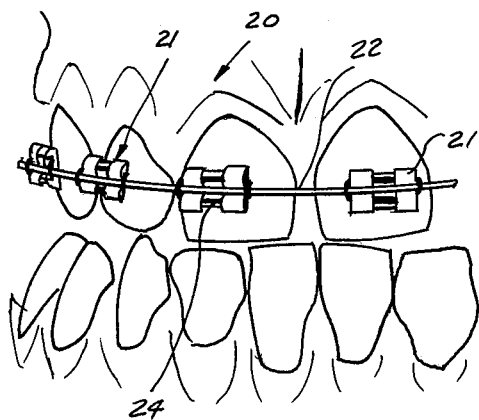
FIG. 1 is a perspective view of teeth braces illustrating how an orthodontic O-ring is applied to a patient's teeth brace.
Figure 2:
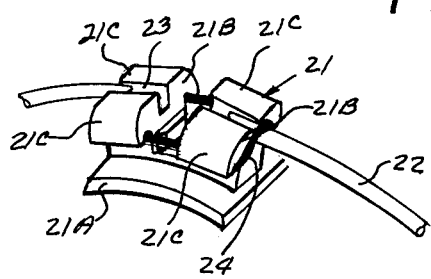
FIG. 2 is a detailed fragmentary perspective view illustrating an orthodontic O-ring as applied to a patient's teeth brace.

Referring to the drawings there is shown in FIG. 1 an orthodontic brace 20 for straightening and/or shifting patient's teeth which comprises a bracket 21 which is bonded directly to each tooth and through which a resilient tensioning wire 22 is strung for tying the respective teeth together. The bracket 21 is firmly attached to a tooth by a suitable adhesive. As best seen in FIG. 2, the bracket 21 comprises a mounting plate 21A which has projecting forwardly therefrom a pair of lugs 21B having oppositely turned ear portions 21C. Extending transversely of the respective eared lugs 21B is a groove 23 for receiving the tensioning wire 22. To secure or attach the tensioning wire 22 within the groove 23 of the projecting lugs 21B, it is customary to utilize very small elastic O-rings 24. As best seen in FIG. 2, the attachment of the wire 22 to the respective teeth brackets 21 is achieved by stretching and looping the O-rings 24 around the projecting lugs 21B so that the wire is maintained in the groove 23 of the bracket in the manner shown in FIG. 2.

Figure 3:
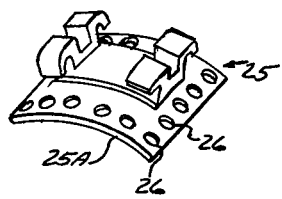
FIG. 3 illustrates a modified bracket construction.

The bracket 25 of FIG. 3 is similar to that of FIG. 2 except that it is formed of a metallic material whereas the bracket construction of FIG. 2 is formed of a plastic material. For this reason the mounting plate 25A of the bracket of FIG. 3 is provided with a series of spaced openings 26 to provide a means whereby the bonding adhesive may flow therethrough to effect a more secure bond of the metallic bracket to a patient's tooth. In all other respects the construction of the metallic bracket 25 of FIG. 3 is similar to that of FIG. 2.

Figure 4:
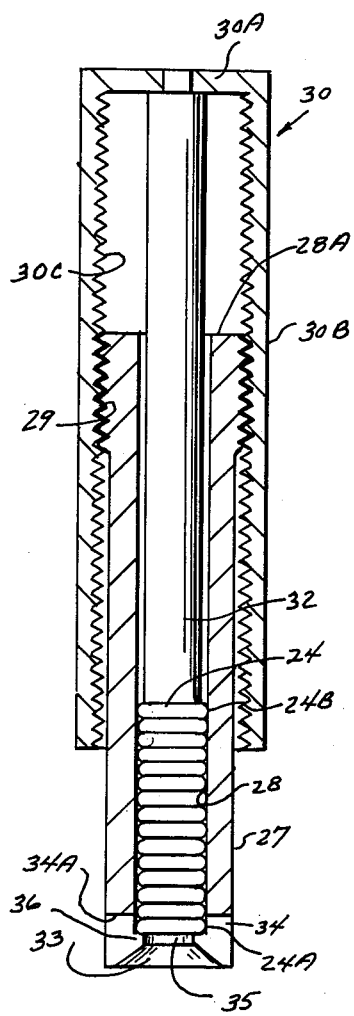
FIG. 4 illustrates a sectional elevation view of an orthodontic O-ring dispenser embodying the present invention.

Because it was heretofore difficult to apply the O-ring 24 to the bracket 21 or 25 secured to a patient's tooth because of the smallness of the respective O-rings and the manner in which they were packaged, there is provided in accordance with this invention an improved orthodontic O-ring dispenser whereby the placement of the O-ring onto the teeth bracket is greatly facilitated. Referring to FIG. 4, there is shown an O-ring dispenser which comprises a tubular housing 27 which is provided with a longitudinal bore 28 extending therethrough. In the form of the invention shown in FIG. 4, one end of the tubular housing 27 is provided with an external threaded portion 29. A closure 30 having a top 30A and depending circumscribing wall 30B, which is internally threaded at 30C is provided to close one end of the bore 28. The arrangement is such that the internally threaded closure 30 circumscribing wall 30B is threadedly engaged to the external threads 29 of the housing. Thus the closure is readily screwed to the housing so that the top 30A can be readily raised and lowered relative to the end of the housing. Connected to the end wall 30A of the cover 30 and arranged to project into the bore 28 of the housing is a plunger 32 which functions to maintain the pressure on a stack of O-rings 24 contained within the bore, and to progressively advance the column of O-rings toward the discharge opening 33 as the O-rings are successively dispensed.

The discharge opening 33 is defined by a transversely extending slot 34 which intersects the bore 28 so as to define an elongated discharge slotted opening 33.

Figure 7A:
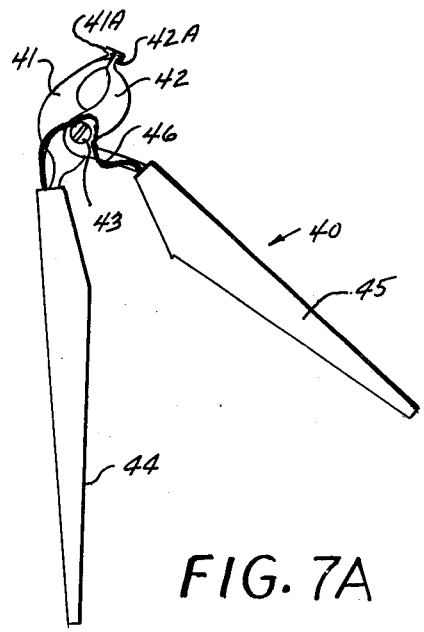
FIG. 7A is a side elevation view of a ligator utilized for effecting the removal of the endmost end ring from the orthodontic O-ring dispenser.
Figure 6:
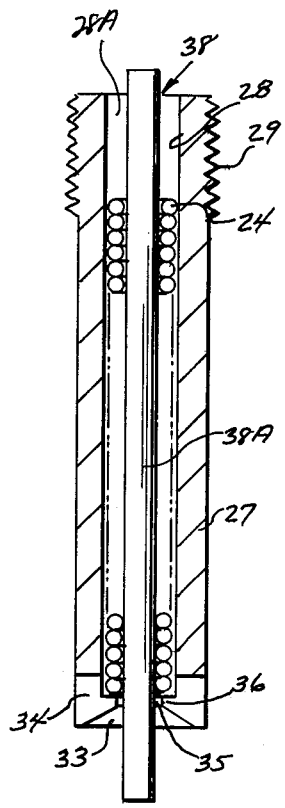
FIG. 6 is a side elevation view in section illustrating how the orthodontic O-ring dispenser is loaded with O-rings.
Figure 7:
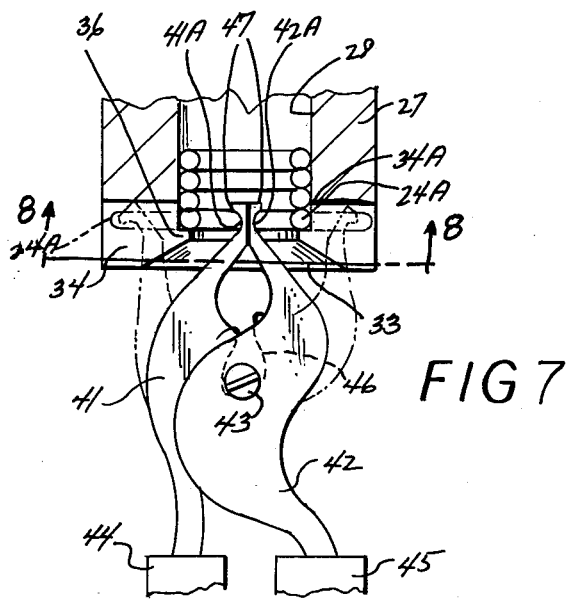
FIG. 7 is a fragmentary view illustrating the manner in which the endmost O-ring is dispensed from the orthodontic O-ring dispenser of FIG. 4.

As best seen in FIGS. 4, 6 and 7, the discharge end of the housing is provided with a tapered countersunk end portion to define a reduced opening 35 which is smaller than the diameter of the bore 28 thus defining a circumscribing inturned lip 36 which functions as a stop for the endmost O-ring 24A in the column of O-rings. The transversely extending slot 34 formed in the end of the housing, as best seen in FIG. 4, has its bottom portion 34A disposed slightly beyond the diameter of the endmost O-ring 24A. As will be hereinafter described, the depth of the slot 34 is such so as to permit the remove or dispensing of only the endmost O-ring 24A, for each dispensing operation as will be hereinafter described.

Figure 5:
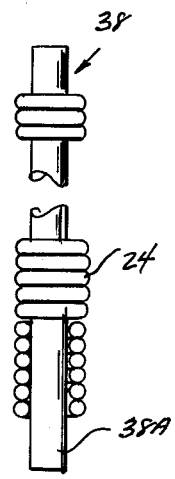
FIG. 5 is an elevation view of a loader utilized for loading the orthodontic O-ring dispenser with the O-rings.

To facilitate the loading of the bore or magazine 28 of the housing 27 with a stack of O-rings 24 there is provided a loader 38. Referring to FIGS. 5 and 6, the loader 38 comprises a rod or shaft 38A on which a series of O-rings 24 are stacked. The diameter of the rod 38A is sized so that the same can be readily inserted through the hole of the O-ring, and the O-rings frictionally secured thereto. With a series of O-rings 24 preloaded on the loading rod 38A, the dentist need simply to insert the rod 38A and loaded O-rings 24 thereon into the inlet end 28A of the housing as best seen in FIG. 6. It will be understood that the end of the loading rod 38A is made sufficiently long and sized so that it will project through the reduced opening 35 at the discharge end of the housing. With the loader 38A and O-rings 24 disposed within the bore 28 of the housing, as seen in FIG. 6, the dentist completes the loading operation by simply pulling the extended end of the loading rod to extract the rod through the dispensing opening. In doing so the inturned lip 36 functions as a stop to prohibit the O-rings from passing through the dispensing opening as the rod 38A is pulled free thereof. With the loading rod 38A thus pulled free of the O-rings 24, the column of O-rings is retained within the magazine or bore 28. The closure end 30 of the magazine housing is then screw threaded onto the end threads 29 of the magazine housing, an amount sufficient for the end of the plunger 32 to bear on the endmost O-ring 24B.

To effect the dispensing of the endmost O-ring 24A, a ligator 40 is provided. As best seen in FIG. 7A the ligator 40 comprises a tool having relatively moveable jaw members 41 and 42 which are pivotally connected for movement between an opened and closed position about a pivot 43. As best seen in FIG. 7A a handle portion 44 and 45 is connected to each of the respective jaw members 41, 42. A spring 46 coiled about the pivot 43 and having its free ends operatively connected to the respective handles 44 and 45 normally biases the jaw members 41, 42 to a normally closed position as indicated in FIG. 7.

Figure 8:
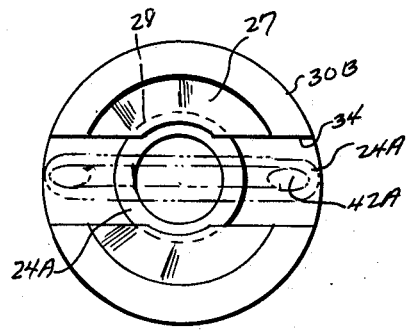
FIG. 8 is an end view illustrating the dispensing of the O-ring from the orthodontic O-ring dispenser taken along line 8—8 on FIG. 7.

In accordance with this invention the respective jaw members 41, 42 as seen in FIG. 7 are each provided with a nose portion 41A, 42A. In the closed position the respective nose portions 41A, 42A are disposed in a butting relationship. The endmost tip of the respective nose portions 41A, 42A of the respective jaws 41, 42 are provided with an outwardly turned nib to define a hook 47 which, in the open position of the jaws, as best seen in the broken in FIG. 7, will function to retain the endmost O-ring 24A thereon. In the closed position, as seen in FIG. 7, the nose portions 41A, 42A, of the jaws 41, 42 form a needle-like projection which can be readily received within the internal diameter or hole of the O-ring. Upon compressing the respective handles 44, 45, of the ligator 40 with the jaws inserted into the dispensing opening, the jaws are spread open so that the endmost end-ring engaged thereby is stretched to a flat oval position as indicated in FIG. 8. By stretching the endmost O-ring 24A to this flat oval position, the O-ring can be readily released or pulled through the slotted discharge opening 34. With the O-ring 24A stretched to a flat oval position upon removal from the dispensing opening, it is simultaneously positioned on the tool so that it can be readily applied by the dentist to the lugs 23 of the tooth bracket 21 for securing the tensioning wire 22 to a patient's tooth so that the dispensing and application of the O-ring can be accomplished in one continuous operation.

FIGS. 9, 10 and 11 illustrate a modified orthodontic O-ring dispenser 50. In this form of the invention the dispenser 50 comprises a tubular housing 51 having a longitudinally extending bore 52 to define a magazine for receiving a stack of elastic orthodontic O-rings 24. As best seen in FIGS. 9 and 10, the discharge end 51A of the dispenser housing 51 is provided with an outwardly projecting tapering or sloping circumscribing surface which terminates in the discharge opening 53.

As best seen in FIG. 11, the tip end 51A of the dispensing housing 51 is provided with intersecting slots 54, 55 which are perfectly disposed at right angles with respect to one another. The intersecting slots 54, 55 thus define a slotted discharge opening through which the O-ring can be dispensed when the endmost O-ring 24A has been stretched to a flat oval position as hereinbefore described. The intersecting slots 54, 55 further define inturned corner portions 56 which define an inturned lip or stop which prohibits the endmost O-ring 24, when disposed within the magazine bore, from normally passing through the discharge opening 53.

As best seen in FIG. 10 the depth of the transverse slot 55, which defines the discharge opening, is made sufficiently deep so as to permit only the endmost ring 24A to be dispensed. Thsu when the ligator is inserted through the dispensing opening to engage the endmost O-ring 24A, only the engaged endmost O-ring 24A can be stretched to a flat oval position so as to effect the removal thereof.

The other end of the magazine bore is sealed or closed by a detachable closure 57. In the illustrated form of the invention, as shown in FIGS. 9 and 10, the end closure 57 comprises a cap having a projecting boss 58 which is externally threaded to complement an internally threaded portion 59 of the magazine bore 52. The dispenser of FIGS. 9 and 10 can be readily loaded with O-rings 24 by the loading technique described with respect to FIGS. 5 and 6.

To maintain a constant compressive force on the stack of O-rings 24 in the magazine 52 of dispenser 50 of FIGS. 9 and 10, and to progressively advance the column of O-rings 24 toward the dispensing opening 53 as each O-ring is successively dispensed, is a spring 60. As best seen in FIGS. 9 and 10 the spring 60 is compressed between the other endmost O-ring 24B and the closure 57. Thus as each O-ring 24 is successively dispensed, the spring 60 elongates so as to advance the column of O-rings toward the discharge opening stops 56 and to maintain the column of O-rings 24 under constant pressure. A spring guide 61 may be connected to the closure 57 to maintain the spring alignment. In all other respects the operation and dispensing of the O-rings 24 from the O-ring dispenser 50, illustrated in FIGS. 9 and 10, is similar to that described with respect to the O-ring dispensers of FIG. 4.

FIGS. 12 and 13 illustrate a modified ligator construction 61. In this form of the invention, the ligator 61 comprises a pair of jaw members 62, 63 which are pivoted for relative movement with respect to one another about a pivot pin 64. Connected to the extended end of the respective jaw members 62, 63 is a handle portion 62A, 63A, a spring means 65, which is pigtailed about the pivot pin 64 and has its free ends in bearing relationship to the respective jaw members 62, 63 so as to normally bias the jaws to the closed position, as best seen in FIG. 12. The respective jaw members 62, 63 are each provided with a nose portion 66 similar to that hereinbefore described with respect to the ligator 40 of FIG. 7A.

In the ligator construction 61 of FIGS. 12 and 13, a latching or locking means is provided for maintaining the jaws 62, 63 in the spread or open position, as indicated in FIG. 13. As best seen in FIGS. 12 and 13, the locking means comprises a slide latch 67 which is recessed on the inner side of one of the handle members, e.g., 62A. The slide latch 67 is operatively connected to a slide actuator 68 which is recessed in the opposite surface portion of a handle 62A, the slide actuators 68 being connected to the sliding latch 67 by a suitable connector, as for example a screw or the like 69. As seen in FIGS. 12 and 13 the connector is moveably mounted in a slot 70 formed in handle 62A to define the limits of movement of the latch 67.

As best seen in FIG. 15, the slide latch 67 is provided with a cut-out portion to define a notch 71 which is adapted to receive or latch onto a catch 72 which is mounted on the contiguous side of the other handle member 63A.

In the illustrated form of the invention as shown in FIG. 12, the catch 72 comprises a headed screw or like fastener. By actuating or sliding the slide latch 67 to the position illustrated in FIG. 13 when the handles are compressed, it will be noted that notch 71 of the slide latch 67 will engage the catch 72. So long as the slide latch 67 is engaged with the catch 72, the jaw members 62, 63 of ligator 61 will be maintained in an open position as indicated in FIG. 13.

To effect the closing of the jaws, the actuator 68 is simply shifted to the opposite position whereupon the notch 71 of slide latch 67 becomes disengaged from the catch 72. In the event that the dentist is interrupted in or during an orthodontic treatment, the ligator described with respect to FIGS. 12 and 13, may be set to its locked position until such time that the orthodontic treatment can be resumed.

FIG. 14 illustrates a further modified O-ring type of dispensing unit 80. In this form of the invention the respective O-rings 24 are integrally molded to a stem or tree 81 in a manner whereby the individual O-rings 24 can be readily separated from the tree or stem 81. As seen in FIG. 14 the stem 81 is made of the same elastic material as are the elastic O-rings 24. The respective O-rings 24 are molded to the stem 81 so as to define a gate or frangible area 82 at the point of connection between the elastic O-ring 24 and the stem or tree 81. As shown in FIG. 14 the frangible area 82 is located as close to the outer periphery of the O-ring as possible. To effect a dispensing of the O-ring 24 from the integrally molded stem or tree 81, the dentist need only to insert the nose portion of the ligator 40 or 61 into the hole of a given O-ring, and by compressing the handles of the ligator to effect the opening of its jaws, the engaged O-ring is stretched to form the flat oval which causes the O-ring to automatically separate from the stem or core 81 along the frangible point or gate 82. Thus the dispensing arrangement of FIG. 14 enables the plastic O-rings 24 to be integrally molded onto a connecting stem or tree in a manner whereby the individual O-rings can be readily successively dispensed upon the dentist's effecting a stretching of the required O-ring with the ligator of the type described with respect to either FIGS. 7A or 12 and 13.

In the form of the invention as shown in FIG. 14, it will be understood that the number of O-rings which can be integrally molded to a single core may be varied as may be considered practical. Also the stem or tree 81 is made sufficiently long so that the tree 81 can be readily wrapped about the dentist's hand so as to be readily accessible and thereby facilitates the picking off of the necessary O-rings as required by the dentist. Since the tree is formed of a readily flexible elastic material, it can be easily wrapped or flexed about the dentist's hand when needed. It is also herein contemplated that the O-rings 24 may be integrally molded onto a loader of the type described with respect to FIGS. 5 and 6. In this latter instance it will be noted that the loading rod 38A avoids the need for the dentist to individually load the O-rings onto the rod prior to loading the magazine of a dispenser 30 or 50. It will be understood that the loading rod 38A becomes a core when a stack of O-rings is molded thereon. Thus when the column or stack of O-rings is molded about the loading rod 38A, the rod may be formed of any suitable material, e.g., it may comprise either a metallic or plastic length of wire or rod.

The orthodontic O-rings 24 to which this invention relates comprise of relatively small elastic O-rings which have an outside diameter of approximately 3 to 4 millimeters. Because of their extremely small size the handling thereof has been difficult. The dispensing apparatus herein described has been noted to greatly facilitate the handling and application of these small orthodontic O-rings.

From the foregoing it will be apparent that the dispensing and application of the O-rings to a tooth bracket 21 during an orthodontic treatment is greatly simplified in that the dispensing operation and the subsequent placement of the O-ring onto the tooth bracket can be effected in a continuous motion, thereby saving the dentist considerable time and effort.

While the instant invention has been described with respect to particular embodiments thereof it will be readily understood that variations and modifications may be made without departing from the spirit or scope of this invention.

I claim:

1. An orthodontic O-ring dispenser comprising:
   a housing having a bore extending therethrough,
   said bore adapted to contain a supply of stacked elastic O-rings,
   said bore having a diameter for accommodating an O-ring adapted to be dispensed therefrom,
   said housing having a rigid non-expandible end portion terminating in a dispensing opening formed at one end of said housing, said opening being in communication with said bore,
   said dispensing opening being defined by a transversely extending slot formed in said end portion,
   said slot having a width which is less than the diameter of an O-ring adapted to be dispensed therefrom,
   means adjacent said slot for defining a stop for said O-ring,
   and means for progressively advancing said stacked O-rings toward said stop means as the endmost O-ring is dispensed by causing said endmost O-ring to be stretched to and form a flat oval permitting it to be removed through said rigid slot.

2. The invention as defined in claim 1 wherein said advancing means includes a closure,
   said closure being moveably mounted on said housing,
   a plunger connected to said closure,
   said plunger extending into said bore to engage with the last of said O-ring in said stack,
   said O-rings being progressively advanced as said closure is moved relative to said housing.

3. The invention as defined in claim 1 wherein said advancing means includes:
   a closure for closing one end of said bore,
   and a spring means interposed between said closure and the last of said O-rings for normally biasing said O-ring toward said dispensing opening.

4. The invention as defined in claim 1 and including a readily removeable loading means for loading a supply of stacked O-rings in said bore whereby said loading means is removed when said O-rings are positioned in said bore.

5. The invention as defined in claim 4 wherein said loading means includes a loading rod having a diameter sized to retain the O-rings thereon.

6. An orthodontic O-ring applicating device comprising:
   a magazine for containing a plurality of flexible elastic O-rings,
   said magazine having a rigid end portion terminating in a dispensing opening,
   said opening being defined as an elongated slot,
   means defining an O-ring stop adjacent said opening,
   said stop normally prohibiting the passages of the O-ring through said slotted opening, and means for effecting the distortion of said O-ring to a flat oval for permitting the passage of the endmost O-ring past said stop means and removal of said endmost O-ring through said slotted opening.

7. The invention as defined in claim 6 wherein said latter means comprises:

a ligator having a pair of relatively moveable jaws, spring means for normally maintaining said jaws closed, said jaws in the normally closed position being adapted to be received in the endmost O-ring adjacent said opening, and handle means connected to said jaws to effect the opening of said moveable jaws, said jaws having an opening movement sufficient to stretch said endmost O-ring to define a flat oval to free it of said stop means and to permit said stretched O-ring to be removed through said slotted opening.

8. The invention as defined in claim 7 and including means for locking the jaws of said ligator in an opened position.

9. The invention as defined in claim 8 wherein said handle means includes a handle connected to the respective jaws, said handles having a side portion adapted to be contiguously disposed in the open jaw position of said ligator, and said lock including a locking latch slideably mounted on the side portion of said handle, and a complementary catch mounted on the contiguous side portion of said other handle, and an actuator connected to said slide latch for shifting said slide latch between a locked and unlocked position relative to said clutch.

* * * * *